(12) United States Patent
Walters et al.

(10) Patent No.: US 8,030,262 B2
(45) Date of Patent: *Oct. 4, 2011

(54) METHODS OF CLEANSING DYED HAIR

(75) Inventors: Russel M. Walters, Philadelphia, PA (US); Anthony J. Cossa, Branchburg, NJ (US); Joseph J. Librizzi, Hillsborough, NJ (US)

(73) Assignee: Johnson & Johnson Consumer Companies, Inc. NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/885,699

(22) Filed: Sep. 20, 2010

(65) Prior Publication Data

US 2011/0008275 A1      Jan. 13, 2011

Related U.S. Application Data

(62) Division of application No. 11/778,704, filed on Jul. 17, 2007, now Pat. No. 7,820,608.

(51) Int. Cl.
| | |
|---|---|
| *A61Q 5/02* | (2006.01) |
| *C11D 3/37* | (2006.01) |
| *C11D 1/29* | (2006.01) |
| *C11D 1/90* | (2006.01) |
| *B08B 3/04* | (2006.01) |
| *A61K 8/72* | (2006.01) |

(52) U.S. Cl. ........ 510/127; 510/155; 510/159; 510/426; 510/434; 510/470; 510/473; 510/476; 510/477; 510/492; 424/401; 424/487; 424/70.5; 424/70.13; 424/70.16; 424/70.22; 424/70.24

(58) Field of Classification Search ................. 510/127, 510/155, 159, 426, 434, 470, 473, 476, 477, 510/492; 424/401, 487, 70.5, 70.13, 70.16, 424/70.22, 70.24
See application file for complete search history.

(56) References Cited

U.S. PATENT DOCUMENTS

| | | |
|---|---|---|
| 4,110,263 A | 8/1978 | Lindemann et al. |
| 4,186,113 A | 1/1980 | Verdicchio et al. |
| 4,215,064 A | 7/1980 | Lindemann et al. |
| 4,233,192 A | 11/1980 | Lindemann et al. |
| 4,263,178 A | 4/1981 | Guth |
| 4,372,869 A | 2/1983 | Lindemann et al. |
| 4,380,637 A | 4/1983 | Lindemann et al. |
| 4,382,036 A | 5/1983 | Lindemann et al. |
| 4,443,362 A | 4/1984 | Guth et al. |
| 4,617,414 A | 10/1986 | Lukenbach et al. |
| 4,726,915 A | 2/1988 | Verdicchio |
| 5,373,044 A | 12/1994 | Adams et al. |
| 5,876,705 A | 3/1999 | Uchiyama et al. |

(Continued)

FOREIGN PATENT DOCUMENTS

DE      10057925 A1      5/2002

(Continued)

OTHER PUBLICATIONS

Chevron Phillips, Specialty Chemicals, "Polyanhydride Resins" [online] 2009 [retrieved on Sep. 25, 2009] from http://cpchem.com/enu/specialtychemicalsployanhydrideresins.asp.

(Continued)

*Primary Examiner* — Brian P Mruk

(57) ABSTRACT

Provided are methods of cleansing dyed hair comprising applying to dyed hair a composition comprising anionic surfactant and a hydrophobically-modified polymer capable of binding surfactant thereto.

7 Claims, 4 Drawing Sheets

U.S. PATENT DOCUMENTS

| | | | |
|---|---|---|---|
| 6,433,061 | B1 | 8/2002 | Marchant et al. |
| 6,642,198 | B2 | 11/2003 | Pflederer et al. |
| 6,737,394 | B2 | 5/2004 | Shana'a |
| 7,157,414 | B2 * | 1/2007 | Librizzi et al. ............... 510/127 |
| 7,754,667 | B2 * | 7/2010 | Walters et al. ............... 510/127 |
| 7,803,403 | B2 * | 9/2010 | Librizzi et al. ............... 424/487 |
| 7,820,608 | B2 * | 10/2010 | Walters et al. ............... 510/127 |
| 2002/0088062 | A1 | 7/2002 | Pratt |
| 2002/0123438 | A1 * | 9/2002 | Pflederer et al. ............. 510/119 |
| 2003/0024059 | A1 | 2/2003 | Pratt |
| 2003/0037385 | A1 | 2/2003 | Slusarewicz |
| 2003/0103929 | A1 * | 6/2003 | Maubru ................... 424/70.16 |
| 2003/0147827 | A1 | 8/2003 | Decoster |
| 2003/0147829 | A1 | 8/2003 | Oldfield et al. |
| 2005/0070452 | A1 | 3/2005 | Librizzi |
| 2005/0075256 | A1 | 4/2005 | Librizzi |
| 2005/0160537 | A1 * | 7/2005 | Watkins et al. ................... 8/405 |
| 2006/0257348 | A1 | 11/2006 | Walters |
| 2006/0280710 | A1 | 12/2006 | Wong |

FOREIGN PATENT DOCUMENTS

| | | |
|---|---|---|
| EP | 1374852 A1 | 1/2004 |
| EP | 1547575 A | 6/2005 |
| WO | WO 03/074021 A1 | 9/2003 |
| WO | WO 03/084499 A2 | 10/2003 |
| WO | WO 2004/006870 A2 | 1/2004 |
| WO | WO 2004/045567 A | 6/2004 |
| WO | WO 2006/121880 * | 11/2006 |

OTHER PUBLICATIONS

Chevron Phillips, MSDS "PA-18" [online] Nov. 8, 2005 [retrieved on Sep. 25, 2009] from http://www.cpchem.com/enu/msds_unsecured/ImportPE0090MSDSENGLISH_AENGLISHAN.pdf.

Bernhofer, et al., *Toxicology In Vitro*, The Influence of the Response of Skin Equivalent Systems To Topically Applied Consumer Products By Epithelial-Mesenchymal Interactions 219-229 (1999).

Carbopol® Aqua SF-1 Polymer, Brilliant Gold Pearlized 2-In-1 Conditioning Shampoo Formulation, Noveon, Inc. CASF1-001, Dec. 2000.

Carbopol® Aqua SF-1 Polymer, Pearlized 2-in-1 Conditioning Shampoo formulation, Noveon, Inc., CASF1-002, Nov. 19, 2001.

Carbopol® Aqua SF-1 Polymer, Clear Shampoo Formulation, Noveon, Inc., CASF1-003, Dec. 2000.

Carbopol® Aqua SF-1 Polymer, Bath Gel with Vitamin E Moisturizing Beads Formulation, Noveon, Inc., CASF1-004, Dec. 2000.

Carbopol® Aqua SF-1 Polymer, Pearlized Mild Body Wash Formulation, Noveon, Inc., CASF1-005, Nov. 19, 2001.

Carbopol® Aqua SF-1 Polymer, Clear Bath Gel (High Betaine) Formulation, Noveon, Inc., CASF1-006, Dec. 2000.

Carbopol® Aqua SF-1 Polymer, Anti-Dandruff Shampoo Formulation, Noveon, Inc., CASF1-007, Dec. 2000.

Carbopol® Aqua SF-1 Polymer, Clear Shampoo/Bath Gel with Beads Formulation, Noveon, Inc., CASF1-008, Mar. 29, 2002.

Carbopol® Aqua SF-1 Polymer, Salicylic Acid Shampoo Formulation, Noveon, Inc., CASF1-009, Dec. 2000.

Carbopol® Aqua SF-1 Polymer, Salicylic Acid Facial Scrub Formulation, Noveon, Inc., CASF1-010, Feb. 25, 2002.

Carbopol® Aqua SF-1 Polymer, Temporary Hair Color shampoo (Medium Brown) Formulation, Noveon, Inc., CASF1-011, Dec. 2000.

Carbopol® Aqua SF-1 Polymer, Antibacterial Liquid Hand Soap with suspended Beads Formulation, Noveon, Inc., CASF1-012, Dec. 2000.

Carbopol® Aqua SF-1 Polymer, Clear Facial Cleanser Formulation, Noveon, Inc., CASF1-013, Dec. 2000.

Carbopol® Aqua SF-1 Polymer, Clear Hydrating Body Wash with Suspended Beads Formulation, Noveon, Inc., CASF1-014, Nov. 19, 2001.

Carbopol® Aqua SF-1 Polymer, Sprayable d-Limonene Waterless Hand Cleaner Formulation, Noveon, Inc., CASF1-015, Jan. 2001.

Carbopol® Aqua SF-1 Polymer, Body Lotion Formulation, Noveon, Inc., CASF1-016, Dec. 2000.

Carbopol® Aqua SF-1 Polymer, Facial Cream Formulation, Noveon, Inc., CASF1-017, Dec. 2000.

Carbopol® Aqua SF-1 Polymer, Alpha Hydroxy Acid Cream Formulation, Noveon, Inc., CASF1-018, Dec. 2000.

Carbopol® Aqua SF-1 Polymer, Pearlized 3-In-1 Conditioning Shampoo Formulation, Noveon, Inc., CASF1-019, Nov. 19, 2001.

Carbopol® Aqua SF-1 Polymer, Clear Shampoo with Microcapsules Formulation, Noveon, Inc., CASF1-020, Dec. 2000.

Carbopol® Aqua SF-1 Polymer, Clear Baby Shampoo Formulation, Noveon, Inc., CASF1-021, Dec. 2000.

Carbopol® Aqua SF-1 Polymer, Economy Pearlized 3-in-1 Conditioning Shampoo Formulation, Noveon, Inc., CASF1-022, Jan. 2001.

Clear Conditioning Shampoo Using Ultrasil™ Q-Plus and Ultrasil™ A-23 Silicones, Noveon, Inc., SIL-019, Dec. 12, 2002.

Clear Bath Gel (High Betaine) Using Carbopol® Aqua SF-1 Polymer, Noveon, Inc., CASF1-024EU, Feb. 10, 2003.

Clear Shampoo/Bath Gel with Beads Using Carbopol® Aqua SF-1 Polymer, Noveon, Inc., CASF1-025EU, Feb. 26, 2003.

Brilliant Gold Pearlized 2-in-1 Conditioning Shampoo Using Carbopol® Aqua SF-1 Polymer, Noveon, Inc., CASF1-026EU, Feb. 26, 2003.

Ethnic Hair Moisturizing Cream With Ultracas™ G-20, Noveon, Inc., SIL-0002, Jun. 28, 2001.

Antibacterial Hand Wash with Moisturizers Using Ultrasil™ DW-18 Silicone, Noveon, Inc., SIL-0005, Mar. 1, 2002.

Mild Conditioning Cream Shampoo, Noveon, Inc., SIL-0017, Dec. 12, 2002.

Moisturizing Shampoo for Ethnic Hair, Noveon, Inc., SIL-0020, Feb. 26, 2003.

Aveeno® Stress Relief Foaming Bath Formulation, Johnson & Johnson Consumer Companies, Inc., 2003.

Aveeno® Daily Moisturizing Foaming Bath Formulation, Johnson & Johnson Consumer Companies, Inc., 2003.

Aveeno® Positively Radiant™ Cleanser Formulation, Johnson & Johnson Consumer Companies, Inc., 2003.

Johnson's® Softwash™ Baby Shampoo Formulation, Johnson & Johnson Consumer Companies, Inc., 2002.

Johnson's® Softwash™ Baby Wash Formulation, Johnson & Johnson Consumer Companies, Inc., 2002.

Johnson's® Soothing Skin Baby Bath Formulation, Johnson & Johnson Consumer Companies, Inc., 2001.

Invittox Protocol No. 86, "The Trans-Epithelial Permeability (TEP) Assay," (May 1994).

Moore, et al., Challenging the surfactant monomer skin penetration model: Penetration of sodium dodecyl sulfate micelles into the epidermis (Journal of Cosmetic Science), Nov. 15, 2002, pp. 29-45.

Moore, et al., Penetration of mixed micelles into the epidermis: Effect of mixing sodium dodecyl sulfate with dodecyl hexa (ethylene oxide) (Journal of Cosmetic Science), 54, 2003, pp. 143-159.

* cited by examiner

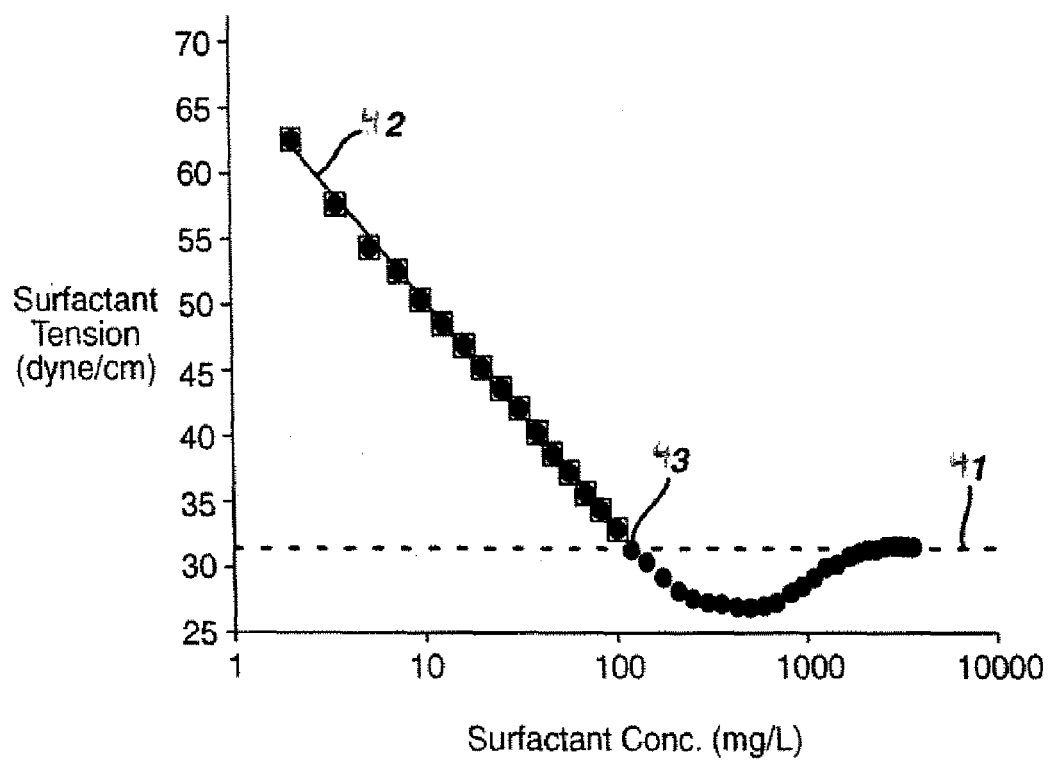

METHODS OF CLEANSING DYED HAIR

CROSS-REFERENCE TO RELATED APPLICATION

This application is a divisional of U.S. application Ser. No. 11/778,704 filed Jul. 17, 2007 (now U.S. Pat. No. 7,820,608), incorporated herein by reference in its entirety.

FIELD OF INVENTION

The present invention relates to methods of cleansing dyed hair. More specifically the invention relates to methods of cleansing dyed hair with improved color retention using a cleanser comprising anionic surfactant and a hydrophobically-modified polymer.

DESCRIPTION OF THE RELATED ART

Applicants have recognized that the color in dyed hair tends to fade over time due, in part, to factors such as exposure to UV and washing of the dyed hair. In particular, a significant amount of hair dye loss is associated with rinsing dyed hair in water alone, and the surfactants present in typical shampoos tend to cause significant additional loss of color during cleansing. Applicants have further recognized that hair dyes are often composed of multiple hair-coloring agents, and each specific coloring agent tends to have a different rate for loss. Therefore, in addition to fading, the color or tone of dyed hair tends to shift due to uneven loss of specific coloring agents.

A variety of attempts to address the need to maintain color/dye on the hair include protecting the hair against UV damage by adding UV filters to shampoo, applying new hair dye daily from a shampoo or conditioner to replace lost hair dye, applying additional materials (conditioners) on top of the hair to reduce hair dye loss during rinsing, and reducing the aggressiveness of the cleansing surfactant by reducing the amount of surfactant and/or using milder surfactant. However, such methods tend to be disadvantageous for a number of reasons including lack of effectiveness in preventing loss of hair-coloring agents, inconsistency in maintaining color or tone, and resulting in compositions that tend to be aesthetically disfavored, for example, compositions with low-foaming and/or poor rheology characteristics.

Accordingly, applicants have identified a need for methods of cleansing hair with improved color retention and/or better aesthetics.

SUMMARY OF THE INVENTION

The present invention provides methods of cleansing dyed hair that overcome the disadvantages of the prior art. According to one aspect, the present invention provides methods of cleansing dyed hair comprising applying to dyed hair a composition comprising anionic surfactant and a hydrophobically-modified polymer capable of binding surfactant thereto.

BRIEF DESCRIPTION OF THE DRAWINGS

FIG. 4 is a graphical depiction of the tensiometry data associated with a composition of the present invention.

DESCRIPTION OF PREFERRED EMBODIMENTS

Figure 1:
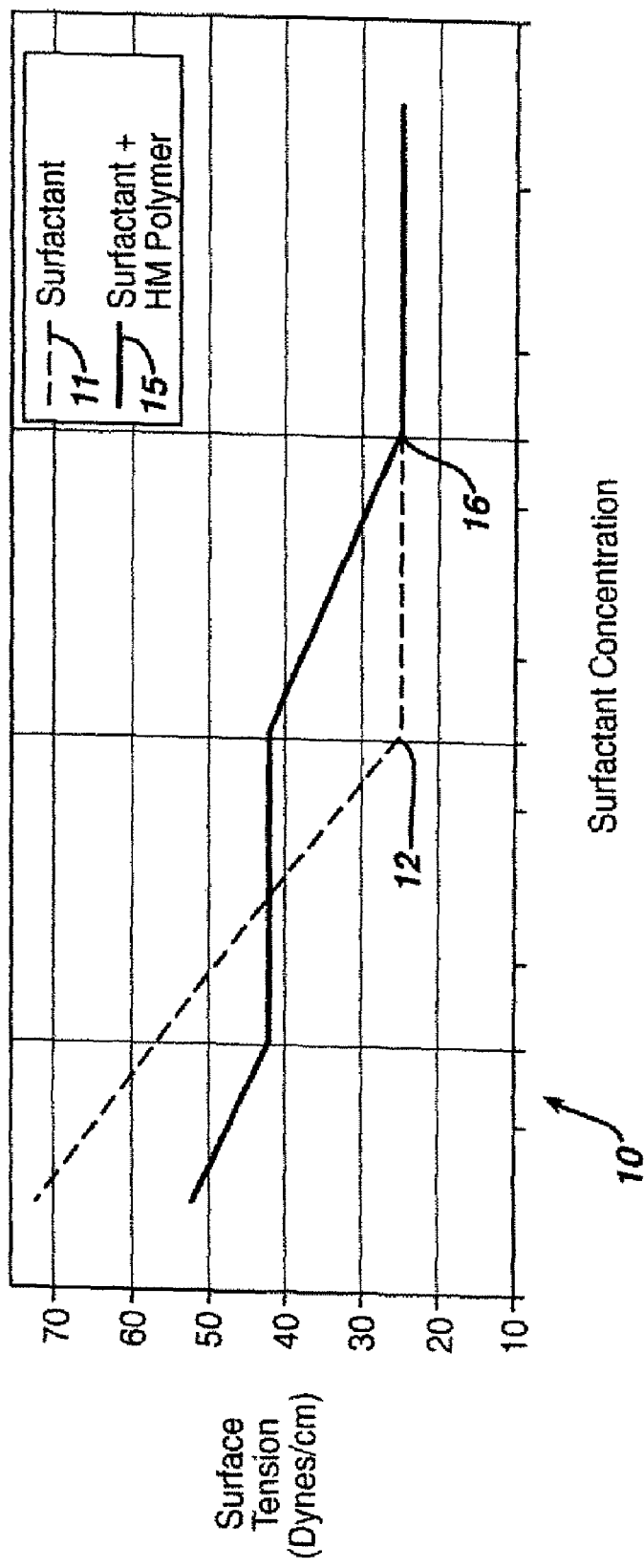
FIG. 1 is a graphical depiction of the idealized tensiometry data associated with the addition of anionic surfactant to two solutions.

As used herein, the term "dyed hair" refers to mammalian hair to which a dye or other coloring agent has been applied to change the color of the hair. As will be recognized by those of skill in the art, any of a variety of dyes and/or coloring agents are suitable for use in coloring hair, including but not limited to naturals dyes, including indigo, logwood, henna (*Lawsonia alba*), walnut hull extraxt, camomile (*Matricaria chamiomila*), and the like, semi-permanent dyes including HC Yellow 2, HC Yellow 5, HC Red 3, HC Blue 2, Disperse Violet 1, Disperse Blue 3, HC Orange 1, HC Red 1, Disperse Black 9, and the like, temporary dyes including FD&C Blue 1, FD&C Red 4, FD&C Yellow 6, EXT D&C Violet 2, and the like, direct action dyes including nitrophenylenediamines, nitroaminophenols, anthraquinones, azo-dyes and C.I. Acid Yellow 1, C.I. Acid Yellow 3, C.I. Acid Orange 7, C.I. Acid Orange, 87, C.I. Acid Red 33, C.I. Acid Violet 43, C.I. Acid Violet 73, C.I. Acid Blue 9, C.I. Acid Blue 168, C.I. Acid Green 25, C.I. Acid Brown 19, C.I. Acid Brown 45, C.I. Acid Black 107, C.I. Basic Yellow 57, C.I. Basic Red 76, C.I. Basic Blue 99, C.I. Basic Brown 16, C.I. Basic Brown 17, Sunset Yellow, Ponceau Red, C.I. Solvent Brown 44, and the like, and any of such dyes/agents and the like, or combinations of two or more thereof, may be applied to hair to achieve "dyed hair".

Applicants have discovered unexpectedly that cleansing compositions comprising anionic surfactant and hydrophobically-modified polymers capable of binding surfactant thereto can be used to cleanse dyed hair with significant improved color retention. For example, applicants have measured the color change and visual fading of dyed hair associated with the use of compositions of the present invention as compared to comparable compositions as further described in the Examples. Applicants have discovered unexpectedly that the present compositions tend to change the color of the dyed hair significantly less than the comparable compositions. In addition, in visual survey data, the present methods result in hair that appears to have faded half as much as hair washed with comparable compositions. Applicants have further discovered that in certain embodiments, the methods of the present invention exhibit cleansing with relatively high-foaming/foam stability properties, and/or other unique characteristics.

Although applicants do not wish to be bound by or to any particular theory of operation, it is believed that the polymeric materials suitable for use in the instant methods act to reduce the stripping of color from dyed hair associated with personal care compositions, at least in part, by binding surfactant (free (unbound) surfactant molecules and/or, especially, surfactant free (unbound) micelles) thereto to reduce the aggressiveness of the surfactant formulation in stripping color from hair. By binding surfactant and/or surfactant micelles thereto, the polymeric materials reduce the concentration of unbound surfactant micelles in a composition and allow for a higher concentration of surfactant to be added to the composition before free micelles are formed and/or before a particular level of aggressiveness is achieved. This desirable shift in the concentration of surfactant is illustrated further in FIG. 1.

FIG. 1 is a graph 10 showing the idealized surface tension data curves associated with the addition of anionic surfactant to two compositions, a composition comprising a hydrophobically-modified material of the present invention and a comparable composition free of hydrophobically-modified material. Curve 11 shows the change in surface tension, measured via conventional tensiometry techniques (examples of which are described hereinbelow), of a composition free of hydrophobically-modified material as increasing levels of anionic surfactant are added thereto. Curve 15 shows the change in surface tension of a composition comprising hydrophobically-modified material as increasing levels of anionic surfactant are added thereto. In curve 11, as surfactant is added to solution, the surfactant tends to populate the liquid/air interface, thus reducing the surface tension of the solution, until essentially the entire surface area is filled. After this point, hereinafter the "critical micelle concentration (CMC)" of surfactant, point 12, essentially all surfactant added to the composition forms free micelles in solution, which formation does not have an appreciable affect on the surface tension of the solution, but tends to increase the irritation associated with the composition. By comparison, as shown in curve 15, as anionic surfactant is added to a solution comprising a hydrophobically-modified material, the surfactant both aligns itself on the liquid/air interface and binds to the hydrophobically-modified material until the CMC, point 16, shifted to a significantly higher surfactant concentration as compared to curve 11, at which point the surfactant added tends to form free micelles.

In light of the above, applicants have recognized that one measure of the efficacy of a particular hydrophobically-modified material in binding surfactant thereto may be expressed as the "Delta CMC" achieved by combining the hydrophobically-modified material with an anionic surfactant to form a reduced irritation composition. A "Delta CMC" as used herein is defined as the number obtained by: (a) determining the CMC for: (i) a particular composition of the present invention comprising anionic surfactant and hydrophobically-modified material, and (ii) the comparable composition of the composition in (i), which CMC values are determined using the Reverse Titration Tensiomtry Test procedures defined in the Examples below; and (b) subtracting the CMC value obtained for composition (ii) from the value obtained for composition (i). In certain embodiments, it is preferred to select a hydrophobically-modified material for use in the present methods such that the Delta CMC associated with the resulting reduced irritation composition is a positive value. In certain more preferred embodiments, the hydrophobically-modified material is selected to achieve a reduced irritation composition having a Delta CMC of about +16 or greater, more preferably, about +80 or greater, and even more preferably of about +300 or greater.

As used herein, the term "hydrophobically-modified polymer" refers generally to any polymer having one or more hydrophobic moieties attached thereto or incorporated therein. Such polymers may be formed, for example, by polymerizing one or more hydrophobic monomers and, optionally, one or more co-monomers, to form a polymer having hydrophobic moieties incorporated therein, and/or also by reacting polymer materials with compounds comprising hydrophobic moieties to attach such compounds to the polymers. Certain hydrophobically-modified polymers and methods of making such polymers are described in U.S. Pat. No. 6,433,061, issued to Marchant et al. and incorporated herein by reference.

Examples of hydrophobically-modified polymers capable of binding a surfactant thereto and suitable for use in the present methods include hydrophobically-modified acrylic polymers, as well as, hydrophobically-modified cellulosics, hydrophobically-modified starches, combinations of two or more thereof, and the like.

Hydrophobically-modified acrylic polymers suitable for use in the present invention may be in the form of random, block, star, graft copolymers, and the like. In certain embodiments, the hydrophobically-modified acrylic polymers are crosslinked, anionic acrylic copolymers. Such copolymers may be synthesized from at least one acidic monomer and at least one hydrophobic ethylenically unsaturated monomer. Examples of suitable acidic monomers include those ethylenically unsaturated acid monomers that may be neutralized by a base. Examples of suitable hydrophobic ethylenically unsaturated monomers include those that contain a hydrophobic chain having a carbon chain length of at least 3 carbon atoms.

In another embodiment, the hydrophobically-modified, crosslinked, anionic acrylic copolymer includes those compositions derived from at least one unsaturated carboxylic acid monomer; at least one hydrophobic monomer; a hydrophobic chain transfer agent comprising alkyl mercaptans, thioesters, amino acid-mercaptan-containing compounds or peptide fragments, or combinations thereof; a cross-linking agent; and, optionally, a steric stabilizer; wherein the amount of said unsaturated carboxylic acid monomer is from about 60% to about 98% by weight based upon the total weight of said unsaturated monomers and said hydrophobic monomer, as set forth in U.S. Pat. No. 6,433,061, which is incorporated by reference herein. In one preferred embodiment, the polymer is an acrylates copolymer that is commercially available from Noveon, Inc. under the tradename, "Carbopol Aqua SF-1." In another preferred embodiment, the hydrophobically-modified acrylic polymer is an associative macromer having a backbone derived from methacrylate and ethylacrylate, and a hydrophobic portion derived from itaconate monomers, which polymer is made via emulsion polymerization. Another preferred polymer comprises an octadecene/methacrylate alternating copolymer, having a molecular weight of from about 20,000 to about 25,000, available from Chevron Phillips Chemical as "PA-18", as well as derivatives of such polymer including hydrolyzed and amidated derivatives, and the like.

Any of a variety of hydrophobically-modified cellulosics or starches are suitable for use in the present invention. Examples of suitable hydrophobically-modified cellulosics include hydrophobically-modified hydroxyethyl cellulose (available commercially, for example, from Hercules Inc. (Wilmington, Del.) as "Natrosol Plus"), and the like. Examples of suitable hydrophobically-modified starches include hydrophobically-modified hydroxylpropyl starch phosphate (available commercially, for example, from National Starch (Bridgewater, N.J.) as "Structure XL"), and the like. Examples of other suitable polymers include hydrophobically-modified polysaccharides, including those derived from cellulose, starch, inulin, guar, xanthan, carragenan, chitosan, pectin, schizophyllan, and the like. Any of such polysaccharides may be nonionic hydrophilic, nonionic hydrophobic, anionic, cationic, zwitterionic, or polymeric.

Any of a variety of hydrophobically-modified inulin polysaccharides are suitable for use herein. Certain preferred hydrophobically-modified polysaccharides include those described generally by the formulas:

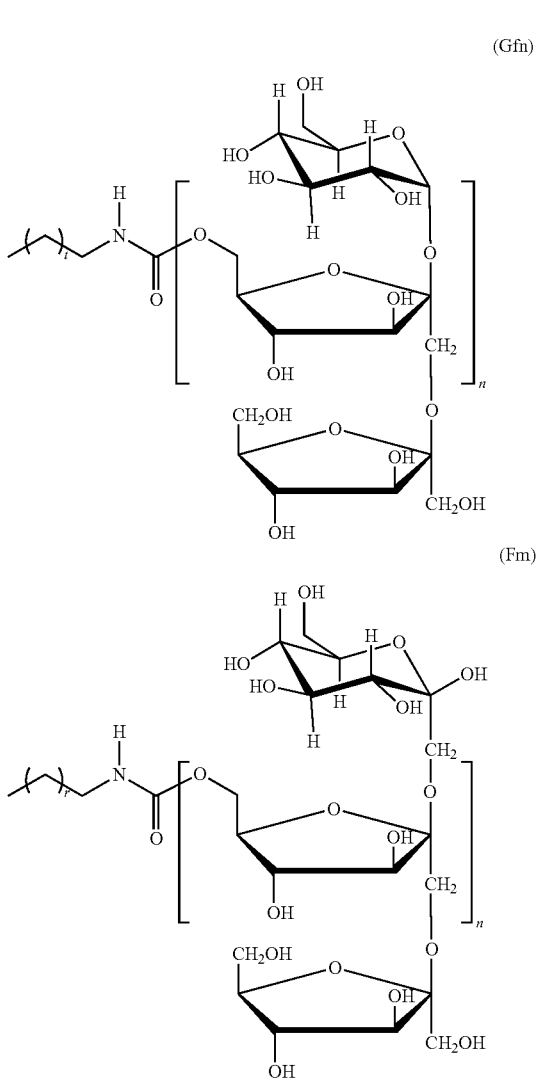

wherein m is about 15-10,000, more preferably about 15-1,000, more preferably about 10-300; n is about 5-10,000, more preferably about 15-1,000, more preferably about 10-300; and r is about 6-30, more preferably about 8-24, and more preferably about 8-18. The hm-inulin is a hm-polyfructose that is extracted from the roots of chicory (*Cichorium intybus*). Naturally according inulin is a polydisperse polysaccharide consisting mainly of β(2-1) fructosyl fructose units with normally, but not necessarily, one glucopyranose unit at the reducing end. The inulin is hydrophobically modified with alkyl groups ($C_4$-$C_{18}$) that are randomly distributed on the sugar backbone on the primary hydroxyl functions as well as on the secondary ones. An example of a preferred inulin polymer is available commercially from Orafti as "Inutec SP-1". The hm-inulin Inutec SP-1 has a degree of polymerization of about 50 and a molecular weight (Mw) of about 5000 g/mol. The hydrophobe alkyl chain on the backbone is a distribution of chain lengths with an average alkyl chain length of about $C_{12}$.

In certain preferred embodiments, the hydrophobically-modified polymers selected for use in the present invention are low molecular-weight polymers. As used herein the term "low molecular weight" polymer refers to a polymer having a weight average molecular weight of less than about 10,000,000 grams per mole ("g/mol"). Certain preferred low molecular weight polymers include polymers having a weight average molecular weight of from about 1,500 to about 10,000,000 g/mol. Certain more preferred low molecular weight polymers include polymers having a weight average molecular weight of from about 2,500 to about 5,000,000 g/mol, more preferably from about 3,000 to about 1,000,000 g/mol, more preferably from about 3,500 to about 500,000. In certain particularly preferred embodiments, the low molecular weight polymers include polymers having a weight average molecular weight of from about 3,500 to about 100,000 g/mol, more preferably about 3,500 to about 60,000 g/mol, in certain embodiments preferably about 5,000 to about 60,000 g/mol, and more preferably from about 15,000 to about 50,000.

Any of a variety of anionic surfactants may be combined with hydrophobically-modified polymeric material to form a composition for use in preferred embodiments of the present methods. According to certain embodiments, suitable anionic surfactants include those selected from the following classes of surfactants: alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof. Examples of certain preferred anionic surfactants include:

alkyl sulfates of the formula

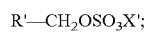

alkyl ether sulfates of the formula

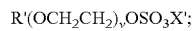

alkyl monoglyceryl ether sulfates of the formula

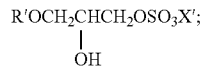

alkyl monoglyceride sulfates of the formula

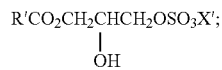

alkyl monoglyceride sulfonates of the formula

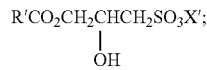

alkyl sulfonates of the formula

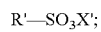

alkylaryl sulfonates of the formula

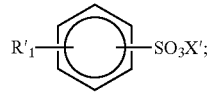

alkyl sulfosuccinates of the formula:

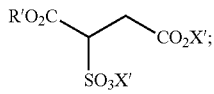

alkyl ether sulfosuccinates of the formula:

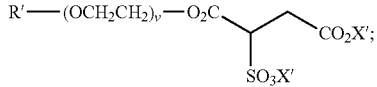

alkyl sulfosuccinamates of the formula:

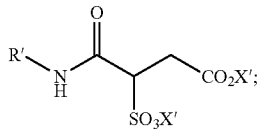

alkyl amidosulfosuccinates of the formula

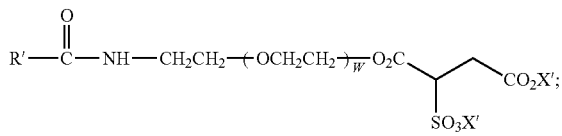

alkyl carboxylates of the formula:

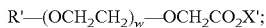

alkyl amidoethercarboxylates of the formula:

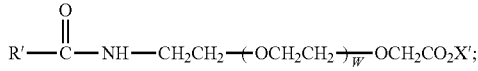

alkyl succinates of the formula:

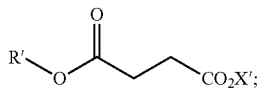

fatty acyl sarcosinates of the formula:

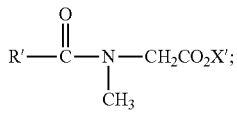

fatty acyl amino acids of the formula:

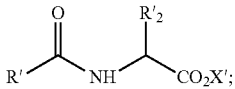

fatty acyl taurates of the formula:

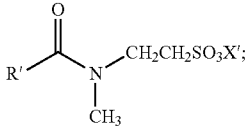

fatty alkyl sulfoacetates of the formula:

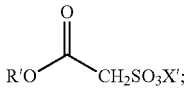

alkyl phosphates of the formula:

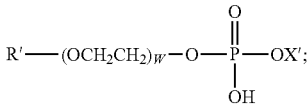

wherein
R' is an alkyl group having from about 7 to about 22, and preferably from about 7 to about 16 carbon atoms,
$R'_1$ is an alkyl group having from about 1 to about 18, and preferably from about 8 to about 14 carbon atoms,
$R'_2$ is a substituent of a natural or synthetic 1-amino acid,
X' is selected from the group consisting of alkali metal ions, alkaline earth metal ions, ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and
v is an integer from 1 to 6;
w is an integer from 0 to 20;
and mixtures thereof.

According to certain embodiments, the anionic surfactant of the present invention preferably comprises one or more alkyl ether sulfates, or mixtures thereof. In certain more preferred embodiments, the anionic surfactant of the present invention comprises sodium trideceth sulfate. Sodium trideceth sulfate is the sodium salt of sulfated ethoxylated tridecyl alcohol that conforms generally to the following formula, $C_{13}H_{27}(OCH_2CH_2)_nOSO_3Na$, where n has a value between 1 and 4, and is commercially available from Stepan Company of Northfield, Ill. under the tradename, "Cedapal TD-403M." Applicants have recognized that sodium trideceth sulfate can be used to particular advantage to obtain compositions having significantly reduced irritation associated therewith according to the present invention.

Any amounts of hydrophobically-modified polymer and anionic surfactants suitable to produce a improved color retention composition may be combined according to the present methods. According to certain embodiments, sufficient hydrophobically-modified material is used to produced a composition comprising from greater than zero to about 5.0% by weight of active hydrophobically-modified material in the composition. Preferably, sufficient hydrophobically-modified material is used to produce a reduced irritation composition comprising from about 0.01 to about 4.0%, more preferably from about 0.3 to about 3.0%, even more preferably from about 0.5 to about 2.5%, and even more preferably from about 0.7 to about 2.0% of active hydrophobically-modified material in the composition. The amount of anionic surfactant used in the present invention is preferably an amount sufficient to produce a composition comprising from about 0.1 to about 30.0%, more preferably from about 1% to about 25.0%, even more preferably from about 3.0 to about 17.0% of total active anionic surfactant in the composition.

The hydrophobically-modified material and anionic surfactant may be combined according to the present invention via any conventional methods of combining two or more fluids. For example, one or more compositions comprising, consisting essentially of, or consisting of at least one hydrophobically-modified material and one or more compositions comprising, consisting essentially of, or consisting of at least one anionic surfactant may be combined by pouring, mixing, adding dropwise, pipetting, pumping, and the like, one of the compositions comprising hydrophobically-modified material or anionic surfactant into or with the other in any order using any conventional equipment such as a mechanically stirred propeller, paddle, and the like. According to certain embodiments, the combining step comprises combining a composition comprising anionic surfactant into or with a composition comprising hydrophobically-modified material. According to certain other embodiments, the combining step comprises combining a composition comprising hydrophobically-modified material into or with a composition comprising anionic surfactant.

The compositions for use in the present methods may further comprise any of a variety of other components nonexclusively including one or more nonionic, amphoteric, and/or cationic surfactants, pearlescent or opacifying agents, thickening agents, secondary conditioners, humectants, chelating agents, and additives which enhance the appearance, feel and fragrance of the compositions, such as colorants, fragrances, preservatives, pH adjusting agents, and the like.

Any of a variety of nonionic surfactants are suitable for use in the present invention. Examples of suitable nonionic surfactants include, but are not limited to, fatty alcohol acid or amide ethoxylates, monoglyceride ethoxylates, sorbitan ester ethoxylates alkyl polyglycosides, mixtures thereof, and the like. Certain preferred nonionic surfactants include polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester. Examples of such preferred polyoxyethylene derivatives of polyol esters include, but are not limited to, PEG-80 sorbitan laurate and Polysorbate 20. PEG-80 sorbitan laurate, which is a sorbitan monoester of lauric acid ethoxylated with an average of about 80 moles of ethylene oxide, is available commercially from ICI Surfactants of Wilmington, Del. under the tradename, "Atlas G-4280." Polysorbate 20, which is the laurate monoester of a mixture of sorbitol and sorbitol anhydrides condensed with approximately 20 moles of ethylene oxide, is available commercially from ICI Surfactants of Wilmington, Del. under the tradename "Tween 20."

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl gluocosides comprise from about 1 to about 6 glucose residues per molecule of alkyl glucoside. A preferred glucoside is decyl glucoside, which is the condensation product of decyl alcohol with a glucose polymer and is available commercially from Henkel Corporation of Hoboken, N.J. under the tradename, "Plantaren 2000."

As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Examples of amphoteric surfactants suitable for use in the present invention include, but are not limited to, amphocarboxylates such as alkylamphoacetates (mono or di); alkyl betaines; amidoalkyl betaines; amidoalkyl sultaines; amphophosphates; phosphorylated imidazolines such as phosphobetaines and pyrophosphobetaines; carboxyalkyl alkyl polyamines; alkylimino-dipropionates; alkylamphoglycinates (mono or di); alkylamphoprionates (mono or di),); N-alkyl β-aminoproprionic acids; alkylpolyamino carboxylates; and mixtures thereof.

Examples of suitable amphocarboxylate compounds include those of the formula:

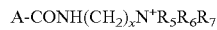

wherein
A is an alkyl or alkenyl group having from about 7 to about 21, e.g. from about 10 to about 16 carbon atoms;
x is an integer of from about 2 to about 6;
$R_5$ is hydrogen or a carboxyalkyl group containing from about 2 to about 3 carbon atoms;
$R_6$ is a hydroxyalkyl group containing from about 2 to about 3 carbon atoms or is a group of the formula:

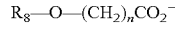

wherein
$R_8$ is an alkylene group having from about 2 to about 3 carbon atoms and n is 1 or 2; and
$R_7$ is a carboxyalkyl group containing from about 2 to about 3 carbon atoms;

Examples of suitable alkyl betaines include those compounds of the formula:

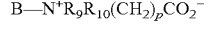

wherein
B is an alkyl or alkenyl group having from about 8 to about 22, e.g., from about 8 to about 16 carbon atoms;
$R_9$ and $R_{10}$ are each independently an alkyl or hydroxyalkyl group having from about 1 to about 4 carbon atoms; and
p is 1 or 2.

A preferred betaine for use in the present invention is lauryl betaine, available commercially from Albright & Wilson, Ltd. of West Midlands, United Kingdom as "Empigen BB/J."

Examples of suitable amidoalkyl betaines include those compounds of the formula:

wherein
D is an alkyl or alkenyl group having from about 7 to about 21, e.g. from about 7 to about 15 carbon atoms;
$R_{11}$ and $R_{12}$ are each independently an alkyl or Hydroxyalkyl group having from about 1 to about 4 carbon atoms;
q is an integer from about 2 to about 6; and m is 1 or 2.

One amidoalkyl betaine is cocamidopropyl betaine, available commercially from Goldschmidt Chemical Corporation of Hopewell, Va. under the tradename, "Tegobetaine L7."

Examples of suitable amidoalkyl sultaines include those compounds of the formula

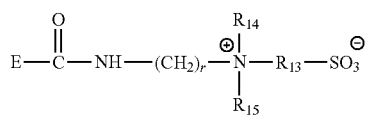

wherein
E is an alkyl or alkenyl group having from about 7 to about 21, e.g. from about 7 to about 15 carbon atoms;
$R_{14}$ and $R_{15}$ are each independently an alkyl, or hydroxyalkyl group having from about 1 to about 4 carbon atoms;
r is an integer from about 2 to about 6; and
$R_{13}$ is an alkylene or hydroxyalkylene group having from about 2 to about 3 carbon atoms;

In one embodiment, the amidoalkyl sultaine is cocamidopropyl hydroxysultaine, available commercially from Rhone-Poulenc Inc. of Cranbury, N.J. under the tradename, "Miratraine CBS."

Examples of suitable amphophosphate compounds include those of the formula:

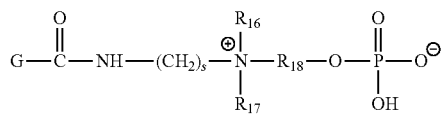

wherein
G is an alkyl or alkenyl group having about 7 to about 21, e.g. from about 7 to about 15 carbon atoms;
s is an integer from about 2 to about 6;
$R_{16}$ is hydrogen or a carboxyalkyl group containing from about 2 to about 3 carbon atoms;
$R_{17}$ is a hydroxyalkyl group containing from about 2 to about 3 carbon atoms or a group of the formula:

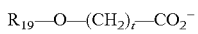

wherein
$R_{19}$ is an alkylene or hydroxyalkylene group having from about 2 to about 3 carbon atoms and t is 1 or 2; and
$R_{18}$ is an alkylene or hydroxyalkylene group having from about 2 to about 3 carbon atoms.

In one embodiment, the amphophosphate compounds are sodium lauroampho PG-acetate phosphate, available commercially from Mona Industries of Paterson, N.J. under the tradename, "Monateric 1023," and those disclosed in U.S. Pat. No. 4,380,637, which is incorporated herein by reference.

Examples of suitable phosphobetaines include those compounds of the formula:

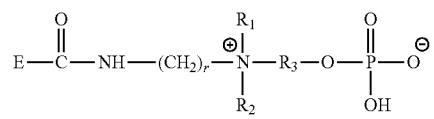

wherein E, r, $R_1$, $R_2$ and $R_3$, are as defined above. In one embodiment, the phosphobetaine compounds are those disclosed in U.S. Pat. Nos. 4,215,064, 4,617,414, and 4,233,192, which are all incorporated herein by reference.

Examples of suitable pyrophosphobetaines include those compounds of the formula:

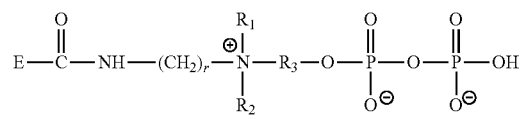

wherein E, r, $R_1$, $R_2$ and $R_3$, are as defined above. In one embodiment, the pyrophosphobetaine compounds are those disclosed in U.S. Pat. Nos. 4,382,036, 4,372,869, and 4,617,414, which are all incorporated herein by reference.

Examples of suitable carboxyalkyl alkylpolyamines include those of the formula:

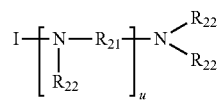

wherein
I is an alkyl or alkenyl group containing from about 8 to about 22, e.g. from about 8 to about 16 carbon atoms;
$R_{22}$ is a carboxyalkyl group having from about 2 to about 3 carbon atoms;
$R_{21}$ is an alkylene group having from about 2 to about 3 carbon atoms and
u is an integer from about 1 to about 4.

Classes of cationic surfactants that are suitable for use in this invention include alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred.

Any of a variety of commercially available pearlescent or opacifying agents which are capable of suspending water insoluble additives such as silicones and/or which tend to indicate to consumers that the resultant product is a conditioning shampoo are suitable for use in this invention. The pearlescent or opacifying agent may be present in an amount, based upon the total weight of the composition, of from about 1 percent to about 10 percent, e.g. from about 1.5 percent to about 7 percent or from about 2 percent to about 5 percent. Examples of suitable pearlescent or opacifying agents include, but are not limited to mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: HO-(JO)$_a$—H, wherein J is an alkylene group having from about 2 to about 3 carbon atoms; and a is 2 or 3; fatty alcohols containing from about 16 to about 22 carbon atoms; fatty esters of the formula: KCOOCH$_2$L, wherein K and L independently contain from about 15 to about 21 carbon atoms; inorganic solids insoluble in the shampoo composition, and mixtures thereof.

The pearlescent or opacifying agent may be introduced to the mild cleansing composition as a pre-formed, stabilized aqueous dispersion, such as that commercially available from Henkel Corporation of Hoboken, N.J. under the tradename, "Euperlan PK-3000." This material is a combination of glycol distearate (the diester of ethylene glycol and stearic acid), Laureth-4 (CH$_3$(CH$_2$)$_{10}$CH$_2$(OCH$_2$CH$_2$)$_4$OH) and cocamidopropyl betaine and may be in a weight percent ratio of from about 25 to about 30: about 3 to about 15: about 20 to about 25, respectively.

Any of a variety of commercially available thickening agents, which are capable of imparting the appropriate viscosity to the personal cleansing compositions are suitable for use in this invention. If used, the thickener should be present in the shampoo compositions in an amount sufficient to raise the Brookfield viscosity of the composition to a value of between about 500 to about 10,000 centipoise. Examples of suitable thickening agents nonexclusively include: mono or diesters of 1) polyethylene glycol of formula: HO—(CH$_2$CH$_2$O)$_z$H, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

Any of a variety of commercially available secondary conditioners, such as volatile silicones, which impart additional attributes, such as gloss to the hair are suitable for use in this invention. In one embodiment, the volatile silicone conditioning agent has an atmospheric pressure boiling point less than about 220° C. The volatile silicone conditioner may be present in an amount of from about 0 percent to about 3 percent, e.g. from about 0.25 percent to about 2.5 percent or from about 0.5 percent to about 1.0 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids.

Any of a variety of commercially available humectants, which are capable of providing moisturization and conditioning properties to the personal cleansing composition, are suitable for use in the present invention. The humectant may be present in an amount of from about 0 percent to about 10 percent, e.g. from about 0.5 percent to about 5 percent or from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, and mixtures thereof; 2)polyalkylene glycol of the formula: HO—(R"O)$_b$—H, wherein R" is an alkylene group having from about 2 to about 3 carbon atoms and b is an integer of from about 2 to about 10; 3) polyethylene glycol ether of methyl glucose of formula CH$_3$—C$_6$H$_{10}$O$_5$—(OCH$_2$CH$_2$)$_c$—OH, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL" and is present in an amount, based upon the total weight of the composition, from about 0 to about 0.5 percent or from about 0.05 percent to about 0.25 percent.

Suitable preservatives include Quaternium-15, available commercially as "Dowicil 200" from the Dow Chemical Corporation of Midland, Mich., and are present in the composition in an amount, based upon the total weight of the composition, from about 0 to about 0.2 percent or from about 0.05 percent to about 0.10 percent.

The compositions produced via the present invention are preferably used as or in personal care products such as shampoos, washes, baths, gels, and the like. As discussed above, applicants have discovered unexpectedly that the instant methods allow for the formulation of such personal care products having improved color retention to dyed hair and, optionally, desirable foaming characteristics.

Any conventional means for contacting dyed hair can be used according to the present invention. The cleansing methods of the present invention may further comprise any of a variety of additional, optional steps associated conventionally with cleansing hair and skin including, for example, lathering, rinsing steps, and the like.

EXAMPLES

The following Examples are illustrative and not intended to be limited in any manner.

Example 1

Two compositions according to embodiments of the present invention (E1-E2) and one comparative composition (C1) are made by combining the ingredients in the amounts listed in Table 1 below as follows:

Each of the compositions of Table 1 was independently prepared as follows: Water (50.0 parts) was added to a beaker. The polymer, (Inutec SP-1 in E15 and E16, and Carbopol Aqua SF1 in C9) was added to the water with mixing. The following ingredients were added thereto independently with mixing until each respective resulting mixture was homogenous: Tegobetaine L7V, Cedepal TD403LD, Tween 20, Promidium LTS, Celquat 230 M, Pheononip and Versene 100XL. The pH of the resulting solution was then adjusted with either a 20% Citric Acid solution or a 20% Sodium Hydroxide.

TABLE 1

| Tradename | INCI Name | C1 w/o polymer | E1 PA-18 | E2 hm-inulin |
|---|---|---|---|---|
| PA-18 (23%) | Octadecene/MA Copoloymer | — | 7.826 | — |
| Inutec SP-1 (100%) | Inulin Lauryl Carbamate | — | — | 1.8 |
| Tegobetaine L-7V (30%) | Cocamidopropyl Betaine | 22.50 | 22.50 | 22.50 |
| Cedepal TD-403LD (30%) | Sodium Trideceth Sulfate | 16.00 | 16.00 | 16.00 |
| Tween 20 | Polysorate-20 | 0.500 | 0.500 | 0.500 |
| Promidium LTS | PEG150 Distearate & PPG-2 Hydroxyethyl Cocamide | 0.750 | 0.750 | 0.750 |
| Celquat 230 M | Polyquaternium 10 | 0.1425 | 0.1425 | 0.1425 |
| Fragrance | Fragrance | 0.2750 | 0.2750 | 0.2750 |
| Pheononip XB | Phenoxyethanol and parabens | 0.600 | 0.600 | 0.600 |
| Versene 100XL | Tetrasodium EDTA | 0.250 | 0.250 | 0.250 |
| NaOH solution (30%) | Sodium Hydroxide | qs | qs | qs |
| Water | Water | qs | qs | qs |

Delta CMC

The Delta CMC associated with compositions E1, E2, and C1 were measured via the Reverse Titration Tensiomtry Test described below and listed in Table 2.

A well-known method to measure the surface tension of surfactant solutions is the Wilhelmy plate method (Holmberg, K.; Jonsson, B.; Kronberg, B.; Lindman, B. *Surfactants and Polymers in Aqueous Solution*, Wiley & Sons, p. 347). In the method, a plate is submerged into a liquid and the downward force exerted by of the liquid on the plate is measured. The surface tension of the liquid can then be determined based on the force on the plate and the dimensions of the plate. It is also well known that by measuring the surface tension over a range of concentrations the critical micelle concentration (CMC) can then be determined.

There are commercially available Wilhelmy plate method instruments. In the following examples, a Kruss K12 Tensiomter (Kruss USA, Mathews, N.C.) with a platinum Wilhelmy plate used to determine the surface tension of each sample over a range of concentrations. The test can be run either forward or reverse. In either case, a sample vessel contains some initial solution in which the Wilhelmy plate measures the surface tension. Then a second solution is dosed into the sample vessel, stirred, and then probed again with the Wilhelmy plate. The solution initially in the sample vessel before the titration begins, into which the second solution is dosed, will be referred to hereinafter as the initial solution, and the solution that is dosed into the sample vessel during the titration will be referred to hereinafter as the dosing solution, in accordance with the convention used by Kruss USA.

In the reverse titration, the concentration of the initial solution is higher than the concentration of the dosing solution. During the reverse titration tests of the following examples, the dosing solution was HLPC grade water (Fischer Scientific, NJ), which had no surfactant, 0 mg/L. The full concentration formulas (for example, those in Table 5) were diluted with HLPC grade water (Fischer Scientific, NJ) to a dilution of approximately 5% wt. This 5% diluted solution was then added to the sample vessel and was the initial solution. The surface tension of this initial solution was measured, and then a volume of the dosing solution was added to the sample vessel. The solution was stirred for at least 5 minutes, before the next surface tension measures was taken. This dosing, stirring, and then measuring was repeated until the dilution reached at least 0.0008%. A Test run according to this procedure is here after referred to as a Reverse Titration Tensiomtry Test.

From the raw tensiomtry data, the CMC was determined for each sample in the following manner. First, the equation for a horizontal line was fitted to the portion of the data at high concentrations, i.e. concentrations above the nadir of the graph and well into the region where the surface tension is essentially constant, as shown, for example, in FIG. 4 as line 41. Then, the equation for a straight line is fit to the data at lower concentrations having a surface tension above the horizontal line derived previously, as shown, for example, in FIG. 4 as line 42. The intersection of these two lines/equations 43 was then defined as the CMC for that sample.

TABLE 2

| Composition | hm-polymer (mg/L) | CMC (mg/L) | Δ CMC (mg/L) |
|---|---|---|---|
| C1 | 0 | 54 | na |
| E1 | PA-18 | 986 | 932 |
| E2 | Inutec SP-1 | 613 | 559 |

Color Retention

The compositions E1, E2, and C1 were tested for color retention when used for washing dyed hair as follows, along with water alone and a comparative commercial product marketed as Pantene Pro-V (hereinafter "C2") containing the ingredients as listed on the label: water, sodium laureth sulfate, sodium lauryl sulfate, cocamidopropyl betaine, sodium chloride, pathenol, panthenyl ethyl ether, lysine HCI, Methyl Tyrosinate HCI, Histidine, Fragrance, Cocamide MEA, Citric Acid, Sodium Benzoate, Tetrasodium EDTA, Methylchloroisthiazolinone, Methylisothiazolinone, Sodium Citrate, Sodijm Xylenesulfonate.

Blonde human hair tresses (10" long and 4" wide) were obtained from DeMeo brothers Inc. (New York, N.Y.). The tresses were dyed with LOREAL Paris® color pulse concentrated color mousse #50 Lively Auburn, following the instructions on the container. After at least 24 hrs, the initial (dyed) color of the tress was measured was the colorimeter.

The original hair tress was then split into 5 tresses (each ¾" wide), and then each tress was washed with a different cleansing formula (water, C1, C2, E1, or E2) according to the washing procedure that follows. First, the tress was rinsed with tap water for 10 seconds (1.5 gal/min @100° F.). Then 0.2 g of the particular formula (water, C1, C2, E1, or E2) was applied for every 1.0 g of hair, and then lathered for 30 s, rinsed for 60 s. The hair tress was combed and blown dry with a Vidal Sassoon® 1250-watt blow dryer set on hi. The washing procedure was repeated and the color was quantified with the spectrophotometer after 0, 1, 4, 9, 14, and 28 washes.

A Hunter Ultra Pro Vis Spectrophotometer® was used to quantify the color of the hair tresses. The spectrophotometer was calibrated with an industry standard; D65 Northern Noon Daylight which equals 6500 Kelvin, the spectrum is 470-680 nm. With the spectrophotometer, measurements were taken twice on each of three locations on the hair tress; top, middle, and lower end of each tress. The quantification of the hair color at each step by the spectrophotometer provided CIE L, a, b, color information. For each washing condition all values collected on each tress were then averaged to yield the L, a, b data for the particular washing condition and formula. Note shown, the data was also analyzed non-aggregated, that is to say, each of the three positions on the tress were compared between formula, and the same trends were observed.

Figure 2:
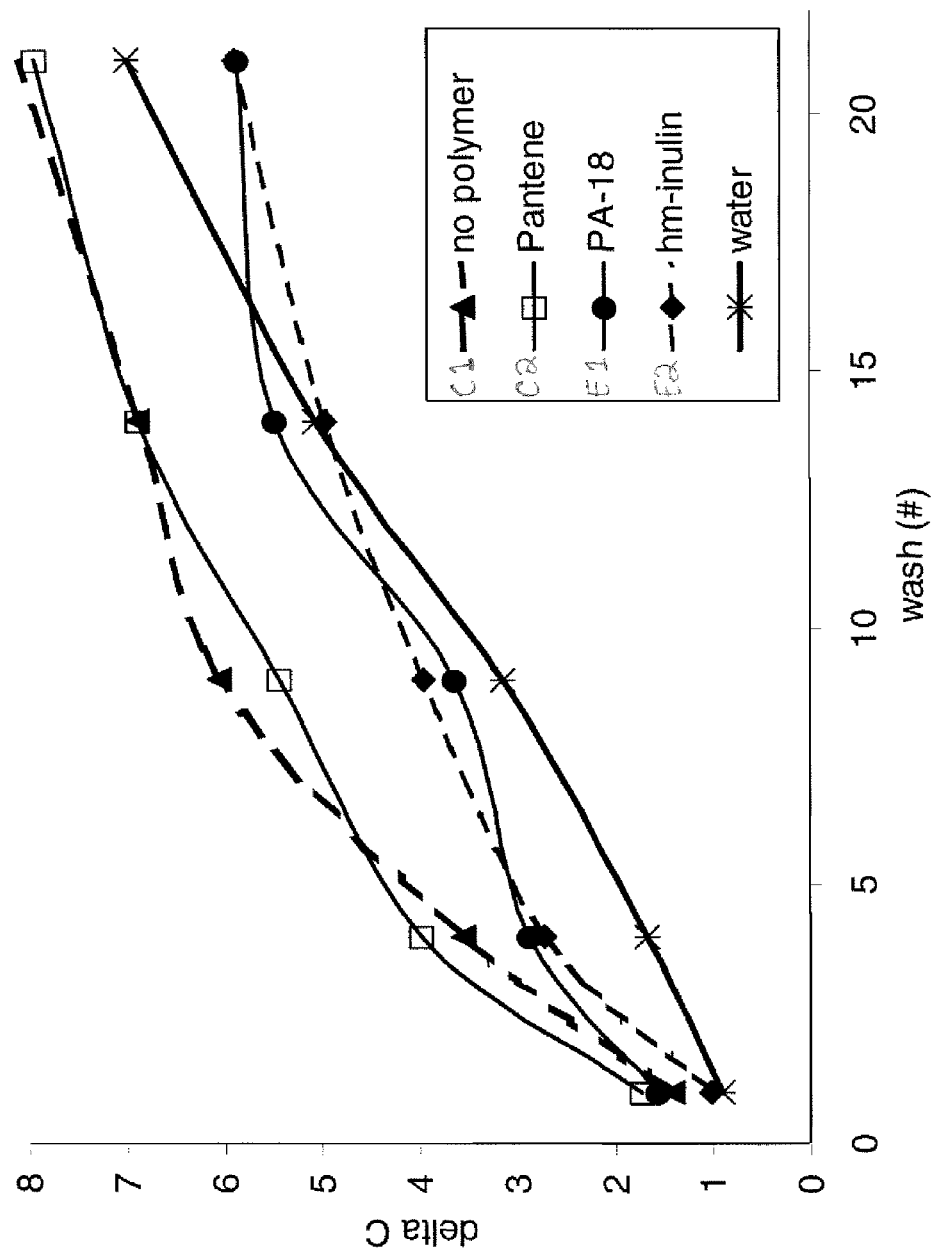
FIG. 2 is a graphical depiction of the relative delta C values measured for certain composition of the claimed invention and comparative compositions.
Figure 3:
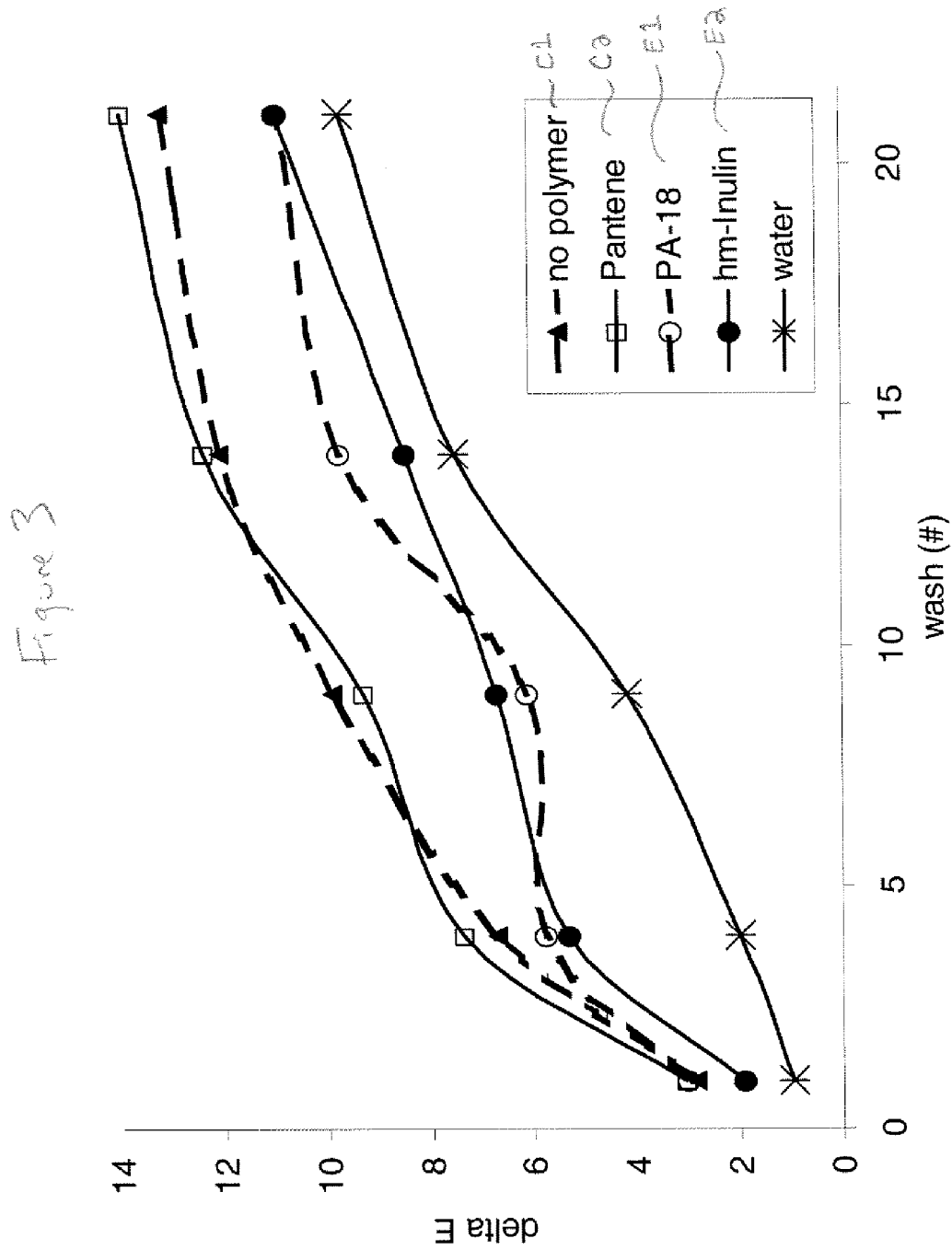
FIG. 3 is a graphical depiction of the relative delta E values measured for certain composition of the claimed invention and comparative compositions.

In order to quantify the color fading that occurred during washing, both the dC, and the dE value was calculated from the L, a, b data for each condition according to the equations:

$$dC_x = \Delta a^2 + \Delta b^2 = (a_0 - a_x)^2 + (b_0 - b_x)^2$$

$$dE_x = \Delta L^2 + \Delta a^2 + \Delta b^2 = (L_0 - L_x)^2 + (a_0 - a_x)^2 + (b_0 - b_x)^2$$

where x is the number of washing cycles, $L_0$ is the initial L after dying, $L_x$ is the L at wash number x, $a_0$ is the initial a after dying, $a_x$ is the a at wash number x, $b_0$ is the initial b after dying, and $b_x$ is the b at wash number x. The results, both dC and dE, are shown in Table 2 after the various washing conditions and illustrated in FIG. 2.

TABLE 2

| # of washes | Water | C2 | C1 | E1 | E2 |
| --- | --- | --- | --- | --- | --- |
| $dE_x$ | | | | | |
| 1 | 1.0 ± 0.6 | 3.1 ± 0.6 | 2.9 ± 0.6 | 3.0 ± 0.8 | 1.9 ± 1.0 |
| 4 | 2.0 ± 0.5 | 7.4 ± 0.3 | 6.7 ± 1.4 | 5.8 ± 1.0 | 5.3 ± 0.7 |
| 9 | 4.2 ± 1.4 | 9.3 ± 0.5 | 9.9 ± 0.0 | 6.1 ± 01.0 | 6.7 ± 0.1 |
| 14 | 7.5 ± 0.5 | 12.4 ± 0.6 | 12.1 ± 0.4 | 9.7 ± 0.6 | 8.5 ± 0.4 |
| 21 | 9.7 ± 0.1 | 14.0 ± 0.7 | 13.2 ± 0.3 | 10.9 ± 0.7 | 10.9 ± 0.6 |
| $dC_x$ | | | | | |
| 1 | 0.9 ± 0.6 | 1.7 ± 0.4 | 1.4 ± 0.5 | 1.6 ± 0.6 | 1.0 ± 0.3 |
| 4 | 1.7 ± 0.4 | 4.0 ± 0.8 | 3.6 ± 0.5 | 2.9 ± 0.5 | 2.7 ± 0.4 |
| 9 | 3.1 ± 0.9 | 5.4 ± 0.5 | 6.0 ± 0.1 | 3.6 ± 0.5 | 3.9 ± 0.2 |
| 14 | 5.0 ± 0.4 | 6.9 ± 0.6 | 6.9 ± 0.2 | 5.5 ± 0.2 | 4.9 ± 0.1 |
| 21 | 7.0 ± 0.1 | 7.9 ± 0.4 | 8.1 ± 0.2 | 5.8 ± 0.3 | 5.8 ± 0.3 |

As shown, the trends in the color change are similar for both dC and dE. In the tress washed with only water there is significant increase in both dE and dC. Tresses washed with either Example C1 or C2 have increases in both dE and dC that are significantly greater than that of water alone. This increase in dE and dC displayed in C1 and C2 is due to the addition dye removed by the surfactant. Surprisingly, the dE and dC value for E1 and E2 at each washing condition was similar to water and significantly lower than the corresponding dE and dC value of C1 and C2. E1 and E2 contain the same amount of surfactant as C1 and a similar amount of surfactant as C2, however E1 and E2 also contain a low Mw hm-polymer in addition to surfactant.

Survey Data, Color Retention

In addition to the instrumental quantification of color change, after the full washing cycle (21 cycles) the tresses were evaluated by 10 people. All tresses were placed on a white cardboard sheet and people were asked to evaluate the color fading of each tress with a score between 1 and 4 (1 least fading and 4 most fading).

TABLE 3

|  | Water | C2 | C1 | E1 | E2 |
| --- | --- | --- | --- | --- | --- |
| 21 washes | 1.1 ± 0.3 | 3.7 ± 0.5 | 3.3 ± 0.5 | 1.6 ± 0.5 | 1.7 ± 0.9 |

The results of the survey, shown in Table 3, correspond well with the color fading result from the spectrophotometer. Again the water displayed the least fading, and significantly more fading was observed from C1 and C2. E1 and E2 exhibited unexpectedly low fading.

What is claimed is:

1. A method of cleansing dyed hair with improved color retention comprising applying to dyed hair a composition comprising at least one anionic surfactant selected from the group consisting of sodium trideceth sulfate, sodium laureth sulfate, and combinations thereof and at least one hydrophobically-modified polymer having a molecular weight of from about 3,500 to about 100,000 selected from the group consisting of hydrophobically-modified starch polymers, hydrophobically modified inulin polymers, and combinations of two or more thereof.

2. The method of claim 1 wherein said composition has a Delta CMC of at least about +80.

3. The method of claim 1 wherein said hydrophobically-modified polymer is a hydrophobically modified starch polymer.

4. The method of claim 1 wherein said hydrophobically-modified polymer is a hydrophobically-modified inulin polysaccharide.

5. The method of claim 1 wherein said composition further comprises at least one amphoteric surfactant.

6. The method of claim 5 wherein said at least one amphoteric surfactant comprises a betaine.

7. The method of claim 1 further comprising the step of rinsing the applied composition from the dyed hair.

* * * * *